United States Patent [19]

Hughes et al.

[11] Patent Number: 5,516,528
[45] Date of Patent: May 14, 1996

[54] DIETARY PHYTOESTROGEN IN ESTROGEN REPLACEMENT THERAPY

[75] Inventors: Claude L. Hughes, Mebane, N.C.; Edna C. Henley, St. Louis, Mo.; Thomas B. Clarkson, Clemmons, N.C.

[73] Assignees: Wake Forest University, Winston-Salem, N.C.; Protein Technologies International, Inc., St. Louis, Mo.

[21] Appl. No.: 372,750

[22] Filed: Jan. 13, 1995

[51] Int. Cl.[6] .............................. A61K 9/20; A61K 9/70; A61K 35/78; A61F 2/02
[52] U.S. Cl. .................. 424/464; 424/423; 424/449; 424/451; 424/195.1; 514/182
[58] Field of Search .................. 424/449, 451, 424/464, 195.1, 423; 514/182

[56] References Cited

U.S. PATENT DOCUMENTS 5,277,910  1/1994  Hiduegi .................. 424/195.1

OTHER PUBLICATIONS

Ursin et al., In: Doll et al., eds., *Cancer surveys—trends in cancer incidence and mortality*, Plainview NY: Cold Spring Harbor Laboratory Press, 241 (1994).

Shimizu et al., *Br. J. Cancer* 63: 963 (1991).

Coward et al., *J. Agr. Food Chem.* 41: 1961 (1993).

Barnes et al., In Jacobs MM, ed., *Diet and Cancer: Markers, prevention and treatment*, New York: Plenum Press, 135 (1994).

Markiewicz et al., *J. Steroid Biochem.* 45; 399 (1993).

Whitten et al., *Steroids* 59: 443 (1994).

Anthony et al., *Circulation* 90: Abstract I-235, Oct. 1994.

*Primary Examiner*—Carlos Azpuru
*Attorney, Agent, or Firm*—Kevin M. Farrell

[57] ABSTRACT

Disclosed is a pharmaceutical composition for oral delivery. The composition includes about 1–2 mg mammalian estrogen and about 25–100 mg phytoestrogen. Compositions of the type described above are utilized, for example, in a therapeutic regimen designed to reduce the risk of coronary heart disease and osteoporosis in postmenopausal women. This method comprises the oral administration of a composition comprising a mixture of estrogen and phytoestrogen, the dosages of mammalian estrogen and phytoestrogen being about 1–2 mg, about 25–100 mg, respectively.

19 Claims, 1 Drawing Sheet

Estradiol

Genistein

Daidzein

FIGURE 1

Estradiol

Genistein

Daidzein

DIETARY PHYTOESTROGEN IN ESTROGEN REPLACEMENT THERAPY

GOVERNMENT SUPPORT

Work described herein was supported by grants from the National Institutes of Health and the United States Government has certain rights in the invention.

BACKGROUND OF THE INVENTION

Coronary heart disease (CHD) is the leading cause of death in women, accounting for 36% of all deaths (approximately 380,000 deaths per year). CHD-related mortality is greater than breast and lung cancer mortality combined. Clinical studies have shown that estrogen replacement therapy (ERT) in the postmenopausal period may reduce morbidity and mortality by 50% or more.

Estrogen deprivation is also an important cause of postmenopausal osteoporosis. Osteoporosis affects about one-third to one-half of all postmenopausal women. Annually, 500,000 vertebral fractures occur. Nearly one-third of women over age 65 will suffer at least one vertebral fracture. Estrogen replacement therapy has been determined to substantially reduce the risk of osteoporosis.

In spite of the reports of substantial reduction in the incidence of both coronary heart disease and osteoporosis associated with estrogen replacement therapy, poor compliance with such therapy has prevented a major impact on women's health overall. Studies have found that the two principal disincentives for women to continue estrogen replacement therapy are fear of breast cancer, and the adverse effects of the progestin (i.e., the nuisance of continuing menstrual periods, cyclic depression, breast tenderness and symptoms like those of premenstrual syndrome) used to prevent endometrial carcinoma. Aside from the breast cancer fear, the other disincentives all relate to the need to use a cyclic or continuous progestin (i.e., medroxyprogesterone acetate) to prevent the risk of endometrial carcinoma.

SUMMARY OF THE INVENTION

The subject invention relates to a pharmaceutical composition for oral delivery. The composition includes about 1–2 mg mammalian estrogen and about 25–100 mg phytoestrogen. In a preferred embodiment, the pharmaceutical composition is in pill or capsule form. The invention also encompasses transdermal or implant delivery systems calibrated to deliver estrogen and phytoestrogen within the previously stated ranges.

Preferably the estrogen is estradiol, and the phytoestrogen is a phytoestrogen which functions as an estrogen antagonist in breast and uterine tissue. Members of the isoflavone class of phytoestrogen (e.g., genistein and daidzein) are particularly preferred.

Compositions of the type described above are utilized, for example, in a therapeutic regimen designed to reduce the risk of coronary heart disease and osteoporosis in postmenopausal women. This method comprises the oral administration of a composition comprising a mixture of estrogen and phytoestrogen, the dosages of mammalian estrogen and phytoestrogen being about 1–2 mg, about 25–100 mg, respectively.

DETAILED DESCRIPTION OF THE INVENTION

Figure 1:
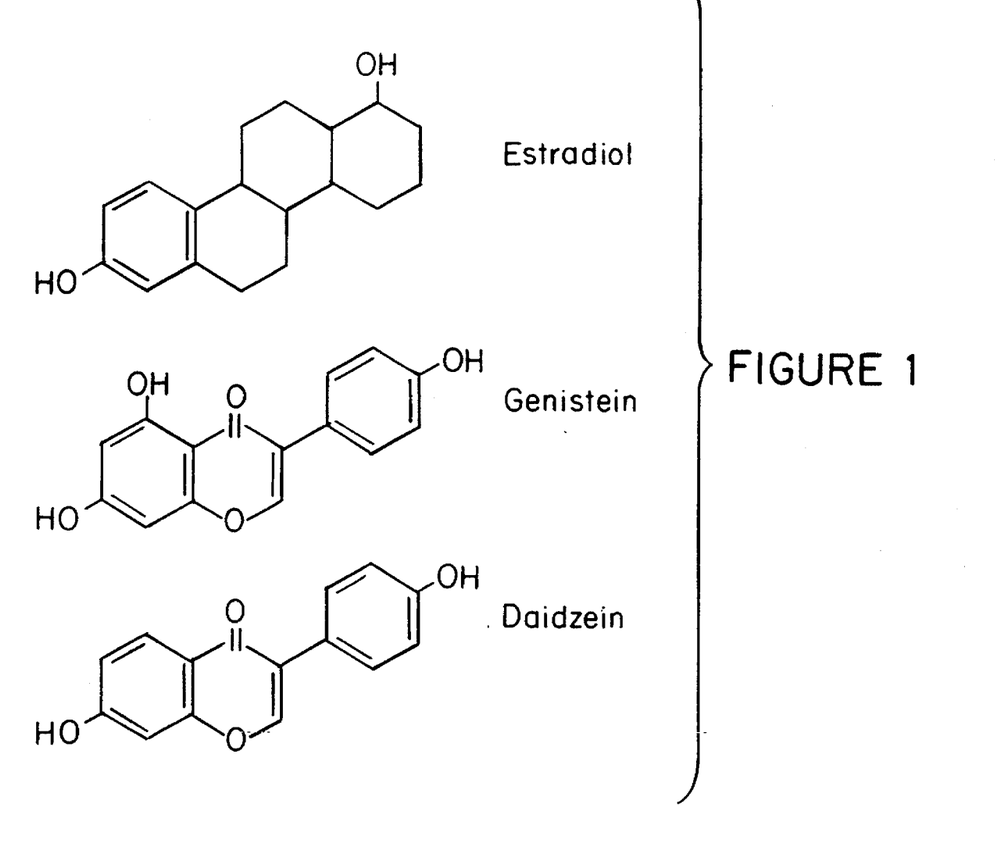
FIG. 1 is a diagram showing the chemical structures of the soy phytoestrogens genistein (4',5,7-trihydroxyisoflavone) and daidzein (4',7-dihydroxyisoflavone) compared with estradiol of mammalian origin.

Nearly 70 years ago, it was reported that certain plants could induce estrus in animals. Subsequently, over 300 plants have been found to possess estrogenic activity (see e.g., Bradbury and White, *Vitamin Horm.* 12:207 (1954), and Farnsworth et al., *J. Pharm. Sci.* 64:717 (1954)). These compounds have been given the general name of "phytoestrogens" and represent several chemical classes. Similarities in the molecular structure of phytoestrogens facilitate binding to the estrogen receptor. An important class of phytoestrogen is the isoflavone class. The chemical structures of the soy isoflavones genistein (4',5,7-trihydroxyisoflavone) and daidzein (4',7-dihydroxyisoflavone) are compared with estradiol of mammalian origin in FIG. 1. Phytoestrogens have been shown to exhibit mixed estrogen agonist-antagonist properties which are organ-specific in vivo (Setchell, In McLachlan, Ed., *Estrogens in the Environment*, New York, Elsevier, pp 69–85 (1985)).

Soybeans are a particularly important source or phytoestrogen. Several hundred varieties or cultivars of soybeans exist, and their phytoestrogen content can vary from 50 mg/100 g to 300 mg/100 g. In addition, given the high levels of consumption of soy protein by certain Oriental cultures, there is a substantial body of relevant epidemiologic evidence. For example, there is epidemiologic evidence that phytoestrogens are associated with lower risk of development of breast and uterine cancer. Oriental women have lower rates of breast cancer compared to Americans. For example, in 1985, the age-adjusted breast cancer incidence in the United States among women aged 35 to 74 was 211.9 per 100,000 women, compared to 69.7 per 100,000 in Japan (Ursin et al., In: Doll et al., eds. *Cancer surveys—trends in cancer incidence and mortality*, Plainview, N.Y.: Cold Spring Harbor Laboratory Press, 241 (1994)). Additionally, Japanese women who have emigrated to the United States are at higher risk of breast cancer than those who remain in Japan, and the risk of cancer in their offspring approaches that of other US-born women (Shimizu et al., *Br. J. Cancer* 63:963 (1991)). Oriental women consume 30 to 50 times more soy products than American women (Coward et al., *J. Agr. Food Chem.* 41:1961 (1993)); as a result, differences in urinary excretion of phytoestrogens between Oriental women and American women are striking (Oriental: 2,000–3,000 nmol/24 hour of genistein and daidzein; American: 30–40 nmol/24 hour). Experimental evidence for lower breast cancer incidence associated with dietary phytoestrogens in soybeans has also been reported (Barnes et al., In Jacobs MM, ed., *Diet and Cancer: Markers, prevention and treatment*, New York: Plenum Press, 135 (1994)). Specifically, dietary soy protein preparations enriched with phytoestrogens inhibited mammary tumors in rats treated with 7,12-dimethyl-benz[a]anthracene compared to rats fed low-phytoestrogen soy protein preparations.

The differences in endometrial cancer incidence between North American (Canadian) and Asian women (Japanese) are also noteworthy. For example, the age-specific endometrial cancer incidence in 1985 increased with age in North America. In contrast, there was no age-associated increase among Japanese women and incidence was lower for each age group compared to North Americans.

The increasingly frequent suggestion that phytoestrogens may protect against development of coronary artery atherosclerosis (CAA) and CHD is based on the evidence that endogenous estrogen protects premenopausal women from CHD relative to men of the same age, that loss of ovarian hormones accounts for the progressing CHD of postmenopausal women, and that estrogen replacement decreases CHD risk among postmenopausal women. That phytoestrogens may be cardioprotective is supported by the low rates of CHD among Oriental people compared to Westerners, and the low rates of CHD among vegetarians compared to omnivorous people, although differences in dietary fat and cholesterol confound these comparisons.

In addition to the epidemiological evidence, recent experimental observations have suggested that phytoestrogens may protect against the development of CAA. For example, studies have shown that male casein-fed rats had significantly higher total plasma cholesterol (TPC) and low density lipoprotein cholesterol (LDL-C) concentrations than soy protein-fed rats. When soybean phytoestrogens were added to casein, the animals had LDL-C concentrations similar to the soy protein-fed group.

In premenopausal female monkeys fed soy protein enriched in phytoestrogens, TPC concentrations were significantly lower and HDL-C concentrations were higher among phytoestrogen-enriched soy protein-fed animals. Furthermore, among surgically postmenopausal female monkeys, HDL-C concentrations were higher (50 versus 67 mg/dl), while TPC concentrations were similar between phytoestrogen-enriched and low-phytoestrogen soy-fed groups.

Finally, among the phytoestrogens, only genistein (the principal phytoestrogen of soybeans) has been the subject of numerous cellular/molecular biologic studies suggesting its potential beneficial effects of several key aspects of CAA, restenosis and arterial function. A summary of those observations is shown in Table 1.

TABLE 1

| Genistein Effects | Reference |
| --- | --- |
| Inhibits interleukin-2 and leukotriene B4 production by mononuclear cells | Atluru et al., Clin. Immunol. Immunopathol. 59:379 (1991) |
| Inhibits platelet-derived growth factor - smooth muscle cell proliferation | Fujio et al., Biochem. Biophys. Res. Commun. 195: 79 (1993) |
| Inhibits aortic fibronectin mRNA expression | Hosoi et al., Circ. Res. 73:689 (1993) |
| Inhibits PDGF c-fos and c-myc proto-oncogene expression in aortic SMC | Nishimura et al., Biochem. Biophy. Res. Commun. 188:1198 (1992) |
| Suppresses tumor necrosis factor and IL-1 secretion by monocytes and T-lymphocytes | See et al., Infect. Inimun. 60:3456 (1992) |
| Inhibits superoxide anion production by stimulated neutrophils | Utsumi et al., Arch. Biochem. Biophys. 294:271 (1992) |
| Inhibits c-jun and c-fos expression by vascular SMC | Zwiller et al., Oncogene 6:219 (1991) |
| Increases nitric oxide expression by macrophages | Dong et al., J. Immunol. 151:2717 (1993). |
| Inhibits endothelin production by endothelial cells | Hu et al., Diabetes 42:351 (1993) |
| Inhibits calcium channel currents in vascular smooth muscle cells | Wijetunge et al., Biochem. Biophys. Res. Commun. 189:1620 (1992) |
| Inhibits thrombin-induced platelet aggregation | Asahi et al., FEBS Lett 309:10 (1992) |

TABLE 1-continued

| Genistein Effects | Reference |
| --- | --- |
| Inhibits platelet-activating factor | Kuruvilla et al., J. Immunol. 151:637 (1993) |
| Inhibits thromboxane-induced platelet aggregation | McNicol et al., Prostaglandins Leukot. Essent. Fatty Acids 48:379 (1993) |

In addition to the evidence discussed above in connection with CHD and CAA, there is also epidemiologic and experimental evidence that phytoestrogen can prevent postmenopausal bone loss and osteoporosis. With respect to the epidemiologic evidence, differences in hip fracture incidence between U.S. women (low phytoestrogen consumers) and Asian women (high phytoestrogen consumers) can not be explained by the usual relationships with calcium consumption. More specifically, the per capita calcium consumption of calcium (mg/day) of U.S. women exceeds 1,000 mg/day, whereas the per capita calcium consumption of Asian women is only slightly above 500 mg/day. However, the incidence of hip fractures per 100,000 women in the U.S. is about 100, whereas the Asian population incidence is only about 22 per 100,000 women.

With regard to the experimental data, a recent report discloses that a low dose, but not a high dose of genistein was equivalent to conjugated equine estrogen (CEE) in maintaining bone mass in ovariectomized rats. Several reports have provided further evidence for a bone-protective effect of genistein. These reports focused on a structurally similar compound, ipriflavone, which is a synthetic 7-isopropoxyisoflavone (Gambacciani et al, *J. Endocrinol. Invest.* 16:333 (1993); Melis et al., In Christiansen C., Riis B., eds, *Proceedings, 4th International Symposium on Osteoporosis and Consensus Development Conference:* 460 (1993); Passeri et al., In Christiansen C., Riis B., eds, *Proceedings, 4th International Symposium on Osteoporosis and Consensus Development Conference:* 463 (1993); Agnusdei et al., In Christiansen C., Riis B., eds, *Proceedings, 4th International Symposium on Osteoporosis and Consensus Development Conference:* 467 (1993)).

The epidemiologic and experimental results discussed above are consistent with a hypothesis that dietary phytoestrogen represents a critical element in the diet of Oriental women which is, at the very least, non-antagonistic of the positive post-menopausal effects of estrogen in bone and cardiac tissue, while functioning antagonistically in breast and uterine tissue. If true, this hypothesis suggests that a dietary regimen designed to produce serum levels of estrogen and phytoestrogen mimicking those of premenopausal Oriental women represents a better alternative to current estrogen replacement therapy. More specifically, the known risks of increased incidence of breast cancer associated with hormone replacement therapy would be reduced by the antagonist effects of phytoestrogen in breast tissue. Similarly, in uterine tissue, the antagonistic effects of phytoestrogen would result in a reduction in the risk of endometrial cancer relative to conventional estrogen replacement therapy. Furthermore, this estrogen antagonistic effect in uterine tissue would obviate the need for the co-administration of progestin. As discussed previously, the side effects of progestin have been identified as a major disincentive with respect to compliance with an estrogen therapy regimen.

Having said this, however, there is contrary experimental evidence which must be considered. More specifically, Wilcox et al. (*Br. Med. J.* 301:905 (1990)) reported increases in vaginal cell proliferation among postmenopausal women consuming soybean phytoestrogens for 6 weeks. In addition, Markiewicz et al. (*J. Steroid Biochem.* 45:399 (1993)) demonstrated experimentally that the soy isoflavone genistein exhibited an estrogen effect on endometrial cancer cells in an in vitro bioassay. These reports are in conflict with the epidemiological and experimental data discussed above.

The subject invention is based on Applicants' discovery that contrary indications in the prior art with respect to vaginal epithelial cell proliferation are not borne out in a carefully controlled study in an animal model system. The animal model selected for initial study was the cynomolgus macaque. Cynomolgus macaque females have physiological and reproductive characteristics similar to those of women (Mahoney CJ, *J. Reprod. Fertil.* 21:153 (1970); MacDonald GJ, *Fertil. Steril.* 22:373 (1971); Jewett DA and Dukelow WR, *J. Reprod. Fertil.* 31:287 (1972)). Like premenopausal women, premenopausal cynomolgus macaque females have significantly higher plasma concentrations of HDL-C than their male counterparts and gender differences in the extent of CAA are like those of human beings during the reproductively active years (Hamm et al., *Atherosclerosis* 48:221 (1983).

As shown in Example 1, the soy isoflavone genistein does not act as an estrogen on the vaginal epithelium. The statistically significant data reported in Example 1 supports the epidemiological and experimental results which indicate that a diet which mimics the diet of Oriental women with respect to isoflavone consumption will reduce the known risks of increased incidence of breast cancer associated with hormone replacement therapy by virtue of the antagonist effects of phytoestrogen in breast tissue. The data also supports the epidemiological and experimental results which indicate that a diet which mimics the diet of Oriental women with respect to isoflavone consumption will reduce the risk of endometrial cancer by virtue of the antagonistic effects of isoflavone resulting in a reduction in the risk of endometrial cancer relative to conventional estrogen replacement therapy. Furthermore, this estrogen antagonistic effect in uterine tissue would obviate the need for the co-administration of progestin. As discussed previously, the side effects of progestin have been identified as a major disincentive with respect to compliance with an estrogen therapy regimen.

Thus, in one aspect the invention relates to a pharmaceutical composition for oral delivery comprising about 1–2 mg mammalian estrogen and about 25–100 mg phytoestrogen. This composition would be administered orally to postmenopausal women. Preferably, the composition would be formulated in pill or capsular form using conventional manufacturing techniques. The preferred mammalian estrogen is estra-1,3,5(10)-triene-3,17β-diol, commonly known as estradiol (e.g., Estrace®, Mead Johnson). The preferred phytoestrogen is selected from the isoflavanoid group. In particular, the isoflavanoids genistein and daidzein have been discussed previously. Transdermal and implant delivery systems calibrated to deliver about 1–2 mg estrogen and about 25–50 mg phytoestrogen/day are also encompassed by the present invention.

The administration of about 1–2 mg mammalian estrogen and about 25–100 mg phytoestrogen to postmenopausal women on a daily basis will serve to decrease the risk of osteoporosis and coronary heart disease, without the need for a co-administered progestin. In light of the fact that the side effects of progestin have been identified as one of the two major disincentives for compliance with estrogen replacement therapy, the present invention represents an estrogen replacement therapy regimen which will meet with increased acceptance and compliance by women. The net effect of increased compliance will be a decrease in coronary heart disease and osteoporosis in postmenopausal women.

EXAMPLES

Example 1

Cynomolgus macaques are similar to women in many aspects of their reproductive physiology. Their endometrial responses to endogenous and exogenous hormones parallel those of women. In this study data from 2 ongoing research projects was used to determine the estrogenic effects of conjugated equine estrogens (CEE), Medroxyprogesterone (MPA), soybean estrogens (SBE) and Tamoxifen on the vaginal epithelium of surgically postmenopausal cynomolgus macaques. In the first study (study one), 40 surgically postmenopausal adult female cynomolgus macaques were randomized to either a control group (OVX) or one of two dietary treatments: CEE at a dose equivalent on a caloric basis to 0.625 mg/woman/day; or SBE at 1.27 mg genistein per g protein. In the second study (study two), 116 surgically postmenopausal adult female cynomolgus macaques were randomized into 5 dietary treatment groups. The five groups were control (OVX), CEE, MPA, CEE+MPA and Tamoxifen. CEE was given at the same dose as in study one and MPA was given at a dose equivalent on a caloric basis to 2.5 mg/woman/day to the MPA and MPA+CEE groups. Tamoxifen was given at a dose equivalent to a woman's dose of 20 mg per day.

Blood samples for study one were collected between May and June 1994 after the animals had been on the treatment for 4 to 6 months. Animals in study two had 5 to 8 blood samples collected over a period of two years on the treatments. Plasma estradiol levels were determined for animals in study one and plasma estradiol and estrone levels were determined for animals in study two to verify the treatments. Vaginal cytology smears were taken after 4 to 6 months of treatment for study one and after 2 years for study two. Maturation Index (MI) was determined using the superficial, intermediate and parabasal cell percentages. Statistical analysis was carried out using ANOVA. For study one the mean MI was 63.3, 66.1 and 98.2 for the OVX (control), SBE and CEE groups respectively. The mean estradiol levels over the treatment period were OVX=3.8, SBE=0, and CEE=147.1. Mean MI and plasma estradiol was significantly greater for animals on CEE compared to the controls or SBE fed animals. The SBE group was not significantly different from the controls. In study two, the mean MI were OVX (control)=67.9, CEE=96.3, MPA=67.8, CEE+MPA= 74.4 and Tamoxifen=81.9. The CEE and Tamoxifen groups had significantly higher MI than the other groups but were not different from each other. The mean estradiol levels were OVX=7.0, CEE=107.3, MPA=10.6, CEE+MPA=109.6 and Tamoxifen=6.0. The CEE and CEE+MPA had significantly higher estradiol than the other groups. The estrone results were similar to the estradiol results with CEE and CEE+ MPA groups having significantly higher levels than the other groups. These results demonstrate that CEE has estrogenic effects on the vaginal epithelium partly mediated through causing an increase in circulating levels of estradiol and estrone. Tamoxifen, an estrogen antagonist in breast tissue, has estrogenic effects on the vaginal epithelium. SBE containing genistein, does not act as an estrogen on the vaginal epithelium. MPA neutralizes the effects of CEE and has no estrogenic effects on the vaginal epithelium.

Example 2

To evaluate the effect of dietary soy among postmenopausal women, ninety-seven women were randomly assigned (in approximately a 3:1 ratio) to a soy diet group after a two-week period when baseline measurements were taken. During the four weeks after randomization, the soy diet group ate daily portions of soy foods (provided by the study) as a substitute for approximately one third of their caloric intake. Members of the control group were instructed to eat "as usual" during the dietary intervention period. All participants were instructed to maintain a stable body weight (weight was recorded daily at home, and four times at a medical clinic). The following markers of estrogenicity were measured at baseline and again at the end of the dietary intervention: serum LH, serum FSH, serum SHBG, and cytology of the vaginal epithelium as reflected by the maturation index or percent superficial cells in vaginal smears. The concentrations of serum estradiol and urinary soy estrogens (urinary daidzein, genistein, and equol) were also measured at baseline and at the end of the diet-intervention period. All laboratory personnel were blinded to the time of collection (pre-diet or end-of-diet) and the treatment status (soy-supplemented diet or control) of all samples assayed. The study began with a pilot phase (n=8 women) and was then completed in two separate sessions, one in the fall (n=40 women) and one in the spring (n=49).

Study participants were volunteers who were recruited from the three-county area around Research Triangle Park, N.C. Recruitment was conducted through newspaper advertisements, fliers at restaurants and health food stores, radio announcements, and specific outreach to vegetarian organizations including Seventh Day Adventist groups. Criteria for entry were: 65 years of age or younger, at least two years past last menses, no use of estrogen replacement therapy or antibiotics in the preceding six months, no use of prescription drugs known to affect outcome measures, e.g., corticosteroids. An intensive participation schedule was required of each woman including weekly meetings, daily first-morning urine collection, four 24-hour urine collections, and four clinic visits to have blood drawn. Each woman received $50/week to compensate for time and travel expenses. This study was approved by the Human Subjects Review Committee at the National Institute of Environmental Health Sciences.

Before randomization the women completed an extensive self-administered questionnaire regarding demographic information, lifestyle factors (exercise, cigarette smoking, coffee drinking, alcohol use), reproductive history, recent use of prescription and nonprescriptive drugs, and an adaptation of the "Health Habits and History Questionnaire" (Block et al., *Am. J. Epid.* 124:453 (1986)) that collects information about dietary habits during the prior year. In addition, women completed a short daily questionnaire on which they recorded their weight, alcohol consumption, cigarette smoking, illnesses, prescription and nonprescription drug use, a set of scaled questions regarding how they felt that day, and (for those in the soy diet group) a record of soy food intake. After the diet intervention period they also filled out a short followup questionnaire to assess any major changes during the study in exercise patterns and (for the control group) diet.

After the first week in the study, daily first-morning urine specimens were collected and frozen at home. They were delivered to study personnel weekly in coolers with freezer packs to keep contents frozen. A 24-hour urine specimen was collected on the same day as the clinic appointment, starting with the second void of the day and ending with the first-morning void (which was placed in a separate container) on the following day. The 24-hour specimens were kept in coolers with previously frozen freezer packs and delivered to study personnel at the end of the 24-hour collection period. Aliquots were frozen and stored at $-20°$ C.

The major daily soy food was a main dish made from whole soybeans or texturized vegetable protein (dried defatted soybean flour). The whole soybeans were a single variety, organically grown, and purchased in a single batch. The texturized vegetable protein (TVP) was purchased in 50 lb. bags from a local health food store. Soy splits (dried soybeans), also from the local health food store, were provided as a daily snack. The soybeans, TVP, and soy splits were analyzed for daidzein and genistein by HPLC-mass spectrometry, as described previously (Setchell et al., *Gastroenterology* 93:225 (1987)). The daily intake of soy consisted of 38 gms of dry TVP (2.1 mg/g daidzein, 0.6 mg/g genistein) or 114 gms of dry whole soybeans (0.7 mg/g daidzein, 0.2 mg/g genistein). In addition, women ate 25 gms of soy splits daily (1.8 mg/g daidzein, 0.7 mg/g genistein). Thus, daily intake of isoflavones was 165 mg/day. This is approximately equivalent on a molar basis to 0.3 mg/day of conjugated steroidal estrogen assuming that the estrogenic activity of the phytoestrogens is about 0.1% that of conjugated estrogen.

Participants visited one of four medical clinics four times during the study: twice in the pre-diet period, and at the end of the diet period. All appointments were scheduled between 8:00 a.m. and 10:00 a.m., and women were instructed to fast from midnight the previous night until after their appointment. At each clinic appointment the women were weighed, and blood was drawn four times at twenty-minute intervals via venipuncture. Blood was centrifuged and equal aliquots of serum from each sample were pooled and stored at $-20°$ C. The pooled serum sample was used for assays in order to reduce the variability caused by the pulsatile release of LH and FSH from the pituitary. At the second pre-diet and final visits, samples of vaginal epithelial cells were taken from the left and right midlateral vaginal walls. Clinical personnel collected cells by making 5–10 scraping strokes with vaginal spatulae. A separate slide was prepared for each wall. Study personnel assisted and immediately sprayed the slides with fixative containing alcohol and polyethylene glycol to preserve cells and prevent drying.

Urinary phytoestrogens (daidzein, genistein, and equol) were measured simultaneously in 5 ml. aliquots of each urine specimen. Isoflavones were extracted from urine by solid-phase extraction after addition of an internal standard $5\alpha$-androstane-$3\alpha$,$17\alpha$-diol (5 µg). Conjugates were hydrolyzed with β-glucuronidase and sulfatase enzymes. Unconjugated estrogens were extracted by liquid-solid extraction, and phenolic compounds were separated from neutral steroid hormone metabolites using an anion exchange gel, triethylaminohydroxypropyl Sephadex LH-20. Trimethylsilyl ethers were prepared, separated by gas chromatography on a DB-1 capillary column, and quantified by mass spectrometry using selected ion monitoring (Setchell et al., *Am. J. Clin. Nutr.* 40:569 (1984)).

Urinary concentrations of soy isoflavones were measured to demonstrate compliance with the diet and to provide a crude measure of phytoestrogen dose for each participant. Earlier work (Setchell et al., *Am. J. Clin. Nutr.* 40:569 (1984)) had shown that urinary equol levels increased by the third day of a soy-supplemented diet, remained high but quite variable during the diet, and returned to low baseline levels by the third or fourth day after cessation of the diet.

To minimize the effect of day-to-day variations in urinary isoflavone levels, first morning urine samples from before the diet (6 ml. aliquots from each of the seven days before randomization) and during the diet period (2 ml. aliquots from each day of the last three weeks of the diet) were pooled prior to phytoestrogen measurement in the pooled sample. Concentrations were expressed relative to the creatinine concentration in the pooled sample. A pilot study of 20 paired specimens had been conducted to measure phytoestrogen concentrations in 24-hour and first-morning urine specimens from the same 24-hour period to verify that first-morning urine specimens (corrected for creatinine) were valid indicators of total urinary excretion.

LH, FSH, SHBG, and estradiol concentrations in sera were measured with commercial kits. Time-resolved fluoroimmunoassays for LH, FSH and SHBG were performed with the appropriate LKB-Wallac DELFIA kits (Electronuclionics, Inc., Columbia, Md.). Estradiol was measured by radio immunoassay (Leeco Diagnostics, Inc., Southfield, Mich.). Samples were analyzed in duplicate and the geometric means of the duplicates were used for analysis. All samples from an individual woman were assayed together. For all analyses, the intra-assay coefficient of variation was <5% and the inter-assay coefficient of variation was <10% based on quality control standards.

All vaginal smear slides were read by a single trained technician. Specimens from each wall were read separately, and the technician was not aware of which slides were paired. From each slide two hundred cells were examined to determine the percentage of parabasal, intermediate, and superficial cells (Hammond, D.O., *Clin. Obstet. Gynaecol* 4: 49 (1977)). The values from the two walls were averaged to give a single value for each woman. Fifty-one (14%) of the 364 slides had too few cells to count and were not included in the calculations. This resulted in four women with no vaginal smear data and 34 women with vaginal smear data based on only one wall for at least one of the time periods. A maturation index was calculated as the percent superficial cells plus half the percent intermediate cells.

The outcome measures in this study were changes during the four-week diet period in serum FSH, LH, SHBG, and vaginal cell maturation index. For maturation index, the change variable was the difference between the end-of-diet value and the baseline value. For FSH, LH, and SHBG, the change variable was the difference in the natural logarithms of the end-of-diet and baseline values, which is equivalent to the logarithms of the ratio: end-of-diet divided by baseline. FSH, LH, and SHBG concentrations were logarithmically transformed before analysis because the transformed values better met normality and equal variance assumptions. Baseline concentrations were estimated as the geometric mean of two pre-diet values.

For each of the four dependent variables (change in FSH, LH, SHBG, and maturation index), tests were conducted for the effect of dietary intervention by including treatment as a term in a basic model that also included season of study, and clinic that the woman attended. Thus, the null hypothesis was that the mean change for the soy diet group was not different from the mean change in the control group. Change in serum estradiol level (difference in natural logarithms of end-of-diet and baseline concentrations), change in weight, and age (by chance, controls were younger on average than women in the soy diet group, though not significantly so) were also added one at a time to the basic model to adjust for possible effects of these factors. Changes in vaginal cytology were examined further by focussing analyses on the percent superficial cells, the cells considered most indicative of estrogen stimulation (Blair, O. M., *Gynecologic Endocrinology:* 159 (1987)). Because only 27 women exhibited a change in superficial cells during the study (most remained at 0%), ordinal logistic regression with three levels of the dependent variable were used: decrease, no change, and increase in percent superficial cells. Adjusting for other variables was done as described above.

In further analyses to explore a possible dose response, treatment as a term in the models was replaced with each of three different measures of urinary soy estrogens: equol concentrations alone, an unweighted sum, or a weighted sum of concentrations with weights of 4 for daidzein, 8 for genistein, and 100 for equol, based on laboratory data on their relative estrogenicity (Shutt, D.A., and Cox, R.I., *J. Endocrinol.* 52:299 (1972); Tang, B. Y., and Adams, N. R., *J. Endocrinol.* 85:291 (1980)).

To evaluate possible interaction effects, i.e., that subsets of the population responded differently to the dietary intervention, terms were added that represented interactions with treatment for age, time since menopause, smoking status, weight, Quetelet's index, and estradiol level at baseline to the models for FSH, LH, SHBG, and maturation index.

Of the ninety-seven women who began the study, three were found to be ineligible (one was still premenopausal, one was taking corticosteroids, and one was taking medication for diabetes). Three others dropped out during the study (two due to emergencies in their families, and one because she could not tolerate the soy foods). The remaining 91 women (66 in the soy diet group and 25 in control group) completed the intake and followup questionnaires, attended all clinic appointments, and collected 24-hour urine samples beginning the morning of their clinic appointment. More than 98% of the requested first-morning urine samples were successfully collected.

Compliance with the diet appeared to be good. Most (73%) reported eating all of their assigned foods. Eighteen women reported having eaten only part of their soy foods on at least one day, but only four women missed days completely (3 missed one day, 1 missed two days), and these occurred at the time of an illness. Consistent with these reports, urinary soy estrogens increased markedly for most women in the soy diet group (average of a 105-fold increase in the unweighted sum), but very little for the controls (average of a 2-fold increase which was not statistically significant). As expected there was little overlap between the control and soy diet groups, but the variation among the women in the soy diet group was broad, with some women showing extremely large increases, others showing more modest changes, and a few showing very little change. Despite efforts to recruit vegetarians, only four participated in the study. The two who were assigned to the soy diet group had low baseline levels and showed large increases in urinary isoflavone concentrations during the diet period.

As instructed, women maintained fairly stable body weights through the diet intervention period. The average weight change was a gain of 0.5 lbs. (0.4 for the diet intervention group and 0.9 for the controls). No one gained or lost more than five pounds and most (82%) varied by no more than two pounds from their baseline weight. Weight change was considered a potential covariate in all analyses. Endogenous estrogen levels, as reflected by serum estradiol concentrations, went down slightly during the study for both the diet-intervention and control groups. The decline was slightly larger for the diet-intervention group than for the controls (1.4 pg/ml vs. 0.9 pg/ml), but not significantly so. Change in estradiol level was considered a potential covariate in all analyses.

Changes over the four-week diet period in serum LH, FSH, SHBG, and in maturation index were determined. Adjustment for season, clinic, age, change in body weight, or change in estradiol concentration had little effect on these relationships. LH and FSH were predicted to decrease with soy intervention, and both did tend to decrease slightly (FSH more so than LH). However, controls also showed small average decreases, and the soy diet and control groups did not differ from each other (p=0.33 for FSH; p= 0.89 for LH). SHBG was predicted to increase with soy intervention, but instead, SHBG tended to decrease for both the soy diet and control groups to a similar degree (p= 0.89). Maturation index was predicted to increase with soy intervention. Though there was a slight average increase in the soy diet group compared to a slight decline in the controls, the groups did not differ significantly (p= 0.40).

When vaginal epithelium data was examined further by focussing on superficial cells (the cells most indicative of estrogen stimulation) the changes were again in the predicted direction (increased superficial cells with dietary intervention). In unadjusted data 43 (68%) women in the soy diet group showed no change in percent superficial cells during the diet, 8 (13%) showed a decrease, and 12 (19%) showed an increase compared with 17 (71%), 5 (21%), and 2 (8%) in the respective categories of the controls ($X^2_{2d.f.}$= 2.03; p=0.36). After adjustment for other factors with ordinal logistic regression, the same trend was determined: in comparison to controls women in the soy diet group tended to have no change or to have their proportion of superficial cells increase during the diet period rather than decrease (Odds Ratio=2.5 (0.8,7.8)), but the difference was consistent with chance (p<0.06).

Urinary levels of the soy estrogens may provide a measure of biologically effective dose for women in the soy diet group. Therefore, evidence for a dose-response relationship between concentrations of urinary soy estrogens and estrogenic responses was evaluated. Concentration of urinary soy estrogens was not a better predictor of the outcome measures than treatment alone, whether the change in soy estrogens was modelled as a linear term or as four separate categories corresponding to quartiles of change. Adjustment for other variables did not affect this result.

Potential interactions were also considered to determine whether subsets of the study participants may have responded to the diet as predicted even though the soy diet group as a whole showed no clear estrogenic responses. Effects that might depend on age, time since menopause, smoking status, weight, Quetelet's index, and estradiol level at baseline were considered. Of the 24 tests conducted, two showed significant interaction effects (p< 0.05). One suggested that the diet/control comparison for change in FSH varied by age. Both soy diet and control groups tended to have small decreases in serum FSH concentrations during the diet period. However, the magnitude of decrease was positively correlated with age in the control group, while there was little variation with age in the diet intervention group. The second interaction suggested that the diet/control comparison for change in SHBG varied by smoking status. Whereas nonsmokers in both soy diet and control groups showed similar small decreases in SHBG, the diet smokers (n=10) and control smokers (n= 5) differed from each other: the smokers in the control group had a small increase in SHBG, and the smokers in the soy diet group had a small decrease. Considering the multiple tests conducted, and that there was no biological basis for predicting such effects, these statistically significant interactions may have resulted from chance.

Example 3

This Example relates to experiments designed to evaluate the beneficial affects of a combined estrogen/phytoestrogen dietary regimen on rats. More specifically, serum lipid profiles, as well as effects on the uterus and bone will be monitored. The architectural and hormonal milieu of the uterus has not been replicated successfully in any alternative to the in vivo model, because the endocrine and paracrine regulators of normal uterus are not completely understood. The small size, short lifespan, and ease of handling make rats ideal for scientific studies. The rat is a well-characterized model species for human diseases and has been used specifically to model uterine cancer. Endometrial hyperplasia can be induced in rats using the doses of Premarin described below. Rats are also well-characterized with respect to serum lipids and lipoproteins and are adequate for assessment of bone density.

Animals will be randomized by body weight into 12 dietary treatment groups of 10 animals each. Nine groups will undergo bilateral ovariectomy (OVX) by 45 days of age, whereas three groups will undergo sham ovariectomy.

TABLE 2

| Group | Diet |
|---|---|
| 1. Low Phytoestrogen + Sham OVX | Low-isoflavone soybean-based diet (equivalent on a caloric basis to 12.05 mg Genistein/woman/day), intact female |
| 2. Low Phytoestrogen + OVX | Low-isoflavone soybean-based diet equivalent to the above diet, ovariectomized female |
| 3. Low Phytoestrogen + OVX + Low Premarin | Low-isoflavone soybean-based diet + Premarin equivalent on a caloric basis to the above diet with the addition of 0.3125 mg Premarin/woman/day |
| 4. Low Phytoestrogen + OVX + High Premarin | Low-isoflavone soybean-based diet + Premarin equivalent on a caloric basis to the above diet with the addition of 0.625 mg Premarin/woman/day |
| 5. High Phytoestrogen + Sham OVX | High-isoflavone soybean-based diet (equivalent on a caloric basis to 117.06 mg Genistein/woman/day), intact female |
| 6. High Phytoestrogen + OVX | High-isoflavone soybean-based diet, ovariectomized female |
| 7. High Phytoestrogen + OVX + Low Premarin | High-isoflavone soybean-based diet + Premarin equivalent on a caloric basis to the above diet with the addition of 0.3125 mg Premarin/woman/day |
| 8. High Phytoestrogen + OVX + High Premarin | High-isoflavone soybean-based diet + 0.625 mg Premarin/woman/day |
| 9. Casein + Sham OVX | Casein-based diet, intact female, no Premarin |
| 10. Casein + OVX | Casein-based diet, ovariectomized female, no Premarin |
| 11. Casein + OVX + Low Premarin | Casein based-diet, ovariectomized female, + 0.3125 mg Premarin/woman/day |
| 12. Casein + OVX + Low Premarin | Casein based-diet, ovariectomized female, +0.625 mg Premarin/woman/day |

In Table 2, doses of hormonal drugs have been computed from clinically used human doses as: human dose/1800 calories/woman/day=dose per calorie of diet. Doses arrived at by this means are, therefore, consistently scaled and are adjusted for metabolic rate. They are similar to the dose which would be arrived at by scaling on the basis of body surface area. The human equivalent isoflavone intake has been estimated by the same equation. Purified diets will be formulated by the Comparative Medicine Clinical Research Center Diet Laboratory. Sufficient isoflavone-rich and isoflavone-poor soy protein is on hand to formulate all diets needed for this study.

Using rats treated as described above, the following hypotheses will be evaluated:

1. Premarin with phytoestrogen will result in lower levels of endometrial hyperplasia in rats relative to Premarin with casein.
2. Premarin with phytoestrogen will retain the bone loss prevention effects of Premarin alone.
3. Casein alone will result in loss of bone mass relative to Premarin and phytoestrogen treated groups.
4. Phytoestrogen diet alone will not cause endometrial hyperplasia relative to Premarin-treated and casein-fed controls.

Example 4

The studies described in this example are intended to examine the separate and combined effects of a traditional estrogen (estradiol) and a soybean phytoestrogen on coronary artery function and reproductive organ pathology in the cynomolgus monkey. Fifty-six adult female cynomolgus monkeys will be selected from the NHLBI breeding colony. All monkeys are consuming a moderately atherogenic diet (0.2 mg cholesterol/Cal of diet) and will continue to consume diets containing the same amount of cholesterol throughout the study.

All monkeys will be ovariectomized, then randomized to 5 treatment groups (n=14 each). Group 1 will receive atherogenic diet with no estrogen replacement and casein will be provided as the source of protein. Group 2 will receive atherogenic diet with 17 beta-estradiol added to the diet at an equivalent dose of 1 mg/day and casein will be provided as the source of protein. Group 3 will receive atherogenic diet, soybean protein (with plant estrogen) as source of protein (equivalent plant dose of 140 mg/day). Group 4 will receive atherogenic diet, estradiol and soybean as the source of protein in the diet. Treatment will be for a period of 5 months.

Prior to necropsy, a number of determinations will be made. Plasma lipid and lipoproteins (i.e., TPC, HDL-C and TG) will be measured once prior to treatment and then 2, 4 and 5 months after treatment. LDL molecular weight will be determined once, 5 months after treatment. Sex hormones (i.e., plasma estradiol, LH and FSH) will be determined once prior to treatment and then 2 months and 5 months after treatment. Plasma genistein concentrations will be measured once, 5 months after treatment. Vaginal Cytology will be done 2 and 5 months after treatment, To determine body fat, ponderosity measurements will be done before and 2 and 5 months after treatment. Serum will be collected and stored for Lp(a) determination.

Monkeys will be anesthetized 2 months after starting treatment and the left iliac artery denuded using a balloon catheter. The procedure will be done aseptically using standardized techniques for "balloon injury".

Immediately prior to necropsy, monkeys will be anesthetized and a catheter advanced from the right femoral artery to the left main coronary artery for measurements of coronary artery diameter using angiographic techniques. Vascular responses of large epicardial coronary arteries will be measured in response to intracoronary infusion of endothelium-dependent and independent agonists. Simultaneous measurements of coronary artery velocity will be done using Doppler techniques to evaluate the effects of treatment on coronary blood flow and reactivity of the coronary microvasculature.

Immediately following the coronary reactivity studies, standard sections of breast tissue, uterus, cervix and vagina will be removed for processing as described below. Routine histology (cell size and character, myometrial thickness and glandular development), estrogen receptor expression, progesterone receptor expression, and Ki-67MIB proliferation marker studies will be done on the tissue. The monkey will then be prepared for whole body perfusion-fixation at physiologic pressure with 10% neutral buffered formalin. The heart will be removed and coronary arteries prepared for histomorphometric analysis. The two common iliac arteries will also be processed for histomorphometric analysis of neointimal formation after balloon injury.

The tissue sections described in the preceding paragraph will be analyzed for: 1) the development of hyperplastic, dysplastic, or neoplastic lesions in breast and endometrium; 2) effects of treatments on estrogen and progesterone receptor status of mammary epithelium and endometrium; and 3) effects of treatment on expression of an endogenous marker of cellular proliferation in mammary and endometrial cells. Hyperplasia and dysplasia will be assessed subjectively and by computer-assisted image analysis of glandular morphology and nuclear size and shape. Estrogen and progesterone receptor status and a marker of cellular proliferation (Ki-67-MIB) will be assessed by immunohistochemistry followed by stereologic quantification of proportions of labeled cells. Parallel pathologic and immunolabeling studies of endometrial responses will be done, allowing a comparative assessment of the two tissues in individual animals.

We claim:

1. A pharmaceutical composition for oral delivery comprising a combination of mammalian estrogen and soy-derived phytoestrogen in an amount sufficient to reduce the risk of coronary heart disease and osteoporosis in women.

2. The pharmaceutical composition of claim 1, wherein the amount sufficient to reduce the risk of coronary heart disease and osteoporosis in women is about 1–2 mg of mammalian estrogen combined with about 25–100 mg phytoestrogen.

3. A pharmaceutical composition of claim 1 which is in pill or capsule form.

4. A pharmaceutical composition of claim 1 wherein the soy-derived mammalian estrogen is estradiol.

5. A pharmaceutical composition of claim 1 wherein the phytoestrogen is an isoflavone.

6. A pharmaceutical composition of claim 5 wherein the isoflavone is genistein.

7. A pharmaceutical composition of claim 5 wherein the isoflavone is daidzein.

8. A method for reducing the risk of coronary heart disease and osteoporosis in women, the method comprising administering orally a combination of mammalian estrogen and soy-derived phytoestrogen in a therapeutically effective amount.

9. The method of claim 8 wherein the therapeutically effective amount is a daily dosage of mammalian estrogen of about 1–2 mg, and soy-derived phytoestrogen of about 25–100 mg.

10. A method of claim 8 wherein the mammalian estrogen is estradiol.

11. A method of claim 8 wherein the soy-derived phytoestrogen is an isoflavone.

12. A method of claim 11 wherein the isoflavone is genistein.

13. A method of claim 11 wherein the isoflavone is daidzein.

14. An estrogen replacement therapy regimen, comprising the oral coadministration of a combination of mammalian estrogen and soy-derived phytoestrogen in a therapeutically effective amount.

15. The estrogen replacement therapy regimen of claim 14 wherein the therapeutically effective amount is a daily dosage of mammalian estrogen of about 1–2 mg, and soy-derived phytoestrogen of about 25–100 mg.

16. A method of claim 14 wherein the mammalian estrogen is estradiol.

17. A method of claim 14 wherein the soy-derived phytoestrogen is an isoflavone.

18. A method of claim 17 wherein the isoflavone is genistein.

19. A method of claim 17 wherein the isoflavone is daidzein.

* * * * *

UNITED STATES PATENT AND TRADEMARK OFFICE
CERTIFICATE OF CORRECTION

PATENT NO. : 5,516,528
DATED : May 14, 1996
INVENTOR(S) : Claude L. Hughes, Edna C. Henley and Thomas B. Clarkson It is certified that error appears in the above-indentified patent and that said Letters Patent is hereby corrected as shown below:

Column 14:

In Claim 48, delete "soy-derived".

In Claim 49, after the word "the", insert ---soy-derived---.

Signed and Sealed this

Fifth Day of November, 1996

*Attest:*

BRUCE LEHMAN

*Attesting Officer*      *Commissioner of Patents and Trademarks*